United States Patent [19]

Inoue et al.

[11] 4,129,778
[45] Dec. 12, 1978

[54] METHOD AND APPARATUS FOR MEASURING THE THICKNESS OF A NON-METALLIC COATING ON A PLATED METAL PLATE

[75] Inventors: Akira Inoue; Minori Oka, both of Tokyo, Japan

[73] Assignee: Kabushiki Kaisha Daini Seikosha, Japan

[21] Appl. No.: 815,019

[22] Filed: Jul. 12, 1977

[30] Foreign Application Priority Data

Jul. 12, 1976 [JP] Japan .................................. 51-82727

[51] Int. Cl.² .................... G01N 23/20; G21K 1/00
[52] U.S. Cl. ..................................... 250/272; 250/273
[58] Field of Search ........................ 250/273, 272, 277

[56] References Cited

U.S. PATENT DOCUMENTS

2,711,480  6/1955  Friedman ............................ 250/273
3,984,679  10/1976  Lublin et al. ........................ 250/272

Primary Examiner—Alfred E. Smith
Assistant Examiner—T. N. Grigsby
Attorney, Agent, or Firm—Robert E. Burns; Emmanuel J. Lobato; Bruce L. Adams

[57] ABSTRACT

The thickness of paint or other non-metallic coating on a galvanized or other plated metal plate is measured by applying radiation to the plated and painted plate and measuring the intensities of fluorescent X-rays thereupon emitted by the plating layer and base plate respectively. The fluorescent X-rays are detected and the electric signal produced by the detector is amplified and shaped to a corresponding waveform. The output of the amplifier is fed to two single channel analyzers and the output signals of the analyzers are counted for a predetermined time period and fed to a computer which computes the thickness from the measured intensities of the emitted fluorescent X-rays.

7 Claims, 2 Drawing Figures

METHOD AND APPARATUS FOR MEASURING THE THICKNESS OF A NON-METALLIC COATING ON A PLATED METAL PLATE

FIELD OF INVENTION

The present invention relates to method and apparatus for measuring the thickness of paint or other nonmetallic layer or coating on plated steel plate.

BACKGROUND OF THE INVENTION

When plated steel plate, for example galvanized plate, is painted while being transported on a belt conveyor it has not been possible to measure the quantity of paint, namely the thickness of paint, applied to the plated steel plate. In order to measure the thickness of the paint on the plated steel plate it has been the practice to stop the conveyor or remove the painted steel plate from the conveyor and measure the thickness of the paint by cutting a dry portion of the paint.

However, it has not been possible to measure the thickness of the paint applied as the steel plate is transported by the conveyor so as to be able to control the quantity of paint being applied to the plate.

It is an object of the present invention to provide a method and apparatus for measuring the thickness of paint on plated steel plate which is painted as it is being transported by a conveyor so as to be able to control the quantity of paint being applied by means of control apparatus, receiving a detecting signal which is detected as the thickness of the paint on the plated steel plate as it is being carried by the conveyor.

The method and apparatus in accordance with the invention are likewise applicable for measuring the thickness of other non-metallic layers, such as wood, polyvinyl or the like, which serve as a membrane coating deposited on the plated metal plate.

In accordance with the invention the thickness of the paint or other coating on the plated steel plate is measured by directing X-rays against the painted steel plate so as to produce fluorescent X-rays emitted from the plating layer and fluorescent X-rays emitted from the base plate, measuring the intensity of the fluorescent X-rays emitted from the plating layer and the intensity of the fluorescent X-rays emitted from the base plate and deriving the thickness of the paint or other coating from these intensities.

Apparatus for carrying out the method of the present invention accordingly comprises an exciting ray source for producing fluorescent X-rays emitted from the plating metal and from the base metal, a detector for detecting the emitted fluorescent X-rays and means for analyzing said X-rays and computing therefrom the thickness of the paint or other coating.

The nature, objects and advantages of the invention will readily be appreciated from the following description when considered in conjunction with the accompanying drawings.

DESCRIPTION OF PREFERRED EMBODIMENT

Figure 1:
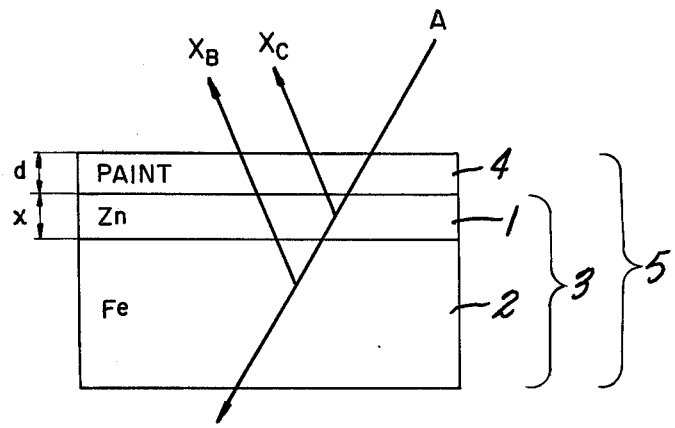
FIG. 1 is a descriptive view illustrating measurement of the thickness of paint or other coating on plated metal in accordance with the invention.

FIG. 1 of the drawings illustrates schematically application of the method in accordance with the present invention to a painted steel plate 5 in which the paint 4 is deposited on a plated metal plate 3 having plating 1 on a base plate 2. For example, the base plate 2 may be of iron or steel and the plating 1 may be zinc. The thickness of the paint 4 is measured on the conveyor which carries the painted steel plate 5.

When the exciting radiation from a source A strikes against the painted steel plate 5 at a selected angle of incidence the fluorescent X-ray $X_B$ of the base plate 2 and the fluorescent X-ray $X_C$ of the plating 1 are emitted from the plated steel plate 3 and the intensity $N_B$ of $X_B$ and the intensity $N_C$ of $X_C$ are affected by the thickness of the plating 1 and of the paint 4. Assuming now that x is the thickness of the plating 1, d is the thickness of the paint 4 and the thickness of the base plate 2 is not limited, $N_B$ and $N_C$ are represented by the following equation:

$$N_B = N^*_B \exp(-\mu_{BC} + \mu_{BP}{}^d) \tag{1}$$

$$N_C = N^*_C [1 - \exp(-\mu_{cc}{}^X)] \exp(-\mu_{CP}{}^d) \tag{2}$$

where $N_B{}^*$ is $N_B$ when $x = d = 0$, $N_C{}^*$ is $N_C$ when $d = 0, x = \infty$, $\mu_{BC}$ is the absorption coefficient to $X_B$ of the plating 1

$\mu_{BP}$ is the absorption coefficient to $X_B$ of the paint 4

$\mu_{CC}$ is the absorption coefficient to $X_C$ of the plating 1

$\mu_{CP}$ is the absorption coefficient to $X_C$ of the paint 4 and $\mu_{BC}$, $\mu_{CC}$, $\mu_{BP}$ and $\mu_{CP}$ are already compensated by the incident angle of the exciting X-ray, the take-off angle of the fluorescent X-ray, the absorption coefficient of the plating 1 to the exciting X-ray, the absorption coefficient of the paint 4, etc.

$N_B{}^*$, $N_C{}^*$, $\mu_{BC}$, $\mu_{BP}$, $\mu_{CC}$ and $\mu_{CP}$ respectively are determined beforehand by using standard samples in which the thickness x and d is already known, or by the value determined theoretically since $N_B{}^*$, $N_C{}^*$, $\mu_{BC}$, $\mu_{BP}$, $\mu_{CC}$ and $\mu_{CP}$ respectively are constant values.

If x is already known, thickness d is determined by either equation (1) or equation (2).

However, it is difficult to know the value of x beforehand and to detect the value of x since the thickness of x of the plating on the steel plate varies considerably in the process in which the steel plate is painted as it is transported in the On-line system.

With respect to the approximate value $d_o$ of d determined by the approximate value $x_o$ of x, the difference $(x_o - x^*)$ affects to the difference $(d_o - d^*)$. Namely, the difference $(x_o - x^*)$ produces an error in the measurement of d when d is determined by either the equation (1) or the equation (2).

The object of this invention is to provide a method of eliminating the measuring error of the thickness d stemming from the above reason.

Accordingly, the object of this invention is to provide a method of measuring the thickness d irrespective of x by solving from the simultaneous equation of the equation (1) and (2) to which the measured intensities $N_B$ and $N_C$ of the fluorescents $X_B X_C$ are provided.

However, d does not solve analytically in case that d is solved by eliminating x from the simultaneous equation of the equations (1) and (2).

The method of solving d from the simultaneous equation of equations (1) and (2) will be explained as follows:

METHOD 1 equation (1) →

$$(N_B/N_B^*) \mu_{CC}/\mu_{BC} = \exp(-\mu_{CC}x) \cdot \exp(\mu_{BP} \cdot \mu_{CC} \cdot d/\mu_{BC}) \tag{3}$$

equation (2) →

$$N_C/N_C^* = [1 - \exp(-\mu_{CC}x)]\exp(-\mu_{CP}d) \tag{4}$$

Assuming that the energy of $X_B$ is approximately equivalent to the energy of $X_C$, and that elements having an absorption difference between the energies of $X_B$ and $X_C$ are not present in the paint or are present only in small quantity, the equation is represented by the following equation:

$$\mu_{BC}/\mu_{CC} = \mu_{BP}/\mu_{CP}$$

Accordingly, in the second exponential function of the right side content of the equation (3), $$\mu_{BP}/\mu_{CC}/\mu_{BC} = \mu_{CP}$$

Accordingly, from the equations (3) and (4), $$(N_B/N_B^*) \mu_{CC}/\mu_{BC} + N_C/N_C^* = \exp(-\mu_{CP}d) \tag{5}$$

$$d = -1/\mu_{CP} \cdot \ln[(N_B/N_B^*)\mu_{CC}/\mu_{BC} + (N_C/N_C^*)] \tag{6}$$

METHOD 2

From the equations (1) and (2), x is solved as shown in the equations (7) and (8):

equation (1) →

$$x = -1/\mu_{BC} [\ln \cdot N_B/N_B^* + \mu_{BP}d] \tag{7}$$

equation (2) →

$$x = -1/\mu_{CC} \cdot \ln[1 - (N_C/N_C^* \exp(-\mu_{CP}d)] \tag{8}$$

Inserting the appropriate value $d_1$ to the equations (7) and (8), the values of x obtained by the computer becomes $x(1)_1$ and $x(2)_1$;

Namely,
    equation (1) → $x(1)_1$ equation (2) → $x(2)_1$

And assuming that $d_i = d_1 + (i-1)\Delta d$ ($i = 1, 2, 3, \ldots$) (where $\Delta d$ is a little value)1 the value of x obtained from the equations (7) and (8) by inserting $d = d_i$ become $x(1)_i$ and $x(2)_i$ equation (1) → $x(1)_i$ equation (2) → $x(2)_i$ And to the positive number $\epsilon$ determined appropriately $$[x(1)_i - x(2)_i] \leq \epsilon \tag{9}$$

and also solve the value of $[x(1)i - x(2)i]$ till satisfying the equation (9) to $i = 1, 2, 3, \ldots$ d is $d_i$ of which i satisfies the equation (9). According to this solving method, the value of d is solved as $d_1$ irrespective of the energy value of $X_B$, the energy value of $X_C$ and the element having the absorption terminal of the energies $X_B$ and $X_C$.

As illustrated in FIG. 1, the incidence angle of the exciting X-ray is that of the arrow A and is an acute angle relative to the baseplate 2 and plating 1. The angle of the fluorescent X-rays $X_B$ and $X_C$ emitted by the base plate 2 and the plating 1 are also acute angles equal to the angle of incidence.

Figure 2:
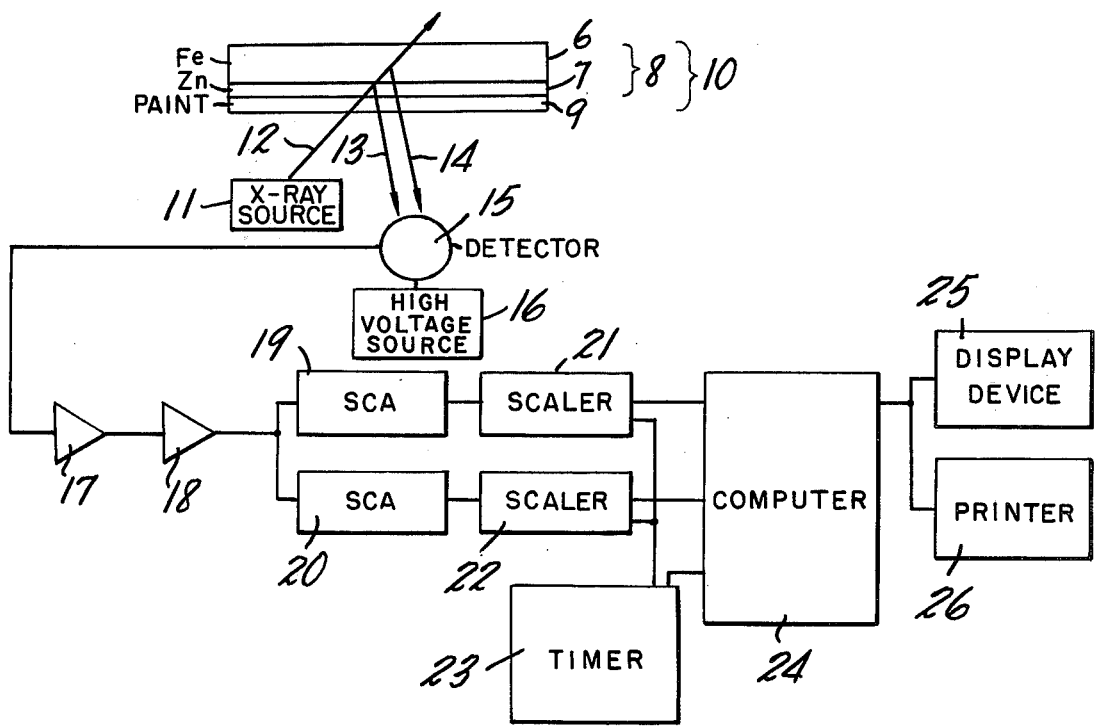
FIG. 2 is a schematic view and circuit diagram illustrating apparatus for carrying out the method of the invention.

Apparatus for carrying out the method of measuring the thickness of paint or other coating or membrane on a plated metal plate, is illustrated by way of example in FIG. 2. The apparatus is shown as comprising a detector 15 such as a proportional counting tube which detects the fluorescent X-ray (Cn - KX) 13 derived from the plating zinc 7 and the fluorescent x-ray (Fe - KX) 14 derived from the iron base plate 6 by impingement of energized radiation ray generated by the energized ray source 11 against the plate 10 comprising a galvanized steel plate 8 painted with paint 9. The detector 15 receives an appropriate voltage derived from a high voltage power source 16.

The electric signal produced by the detector 15 is amplified by a pre-amplifier 17 and is formed into a wave form by the linear amplifier 18.

The output signal of the linear amplifier 18 is applied to single channel analyzers (hereinafter called SCA) 19 and 20. SCA 19 is adjusted so as to produce a normalized electric pulse signal at the output terminal thereof when SCA 19 receives the electric pulse signal corresponding in pulse height to (Fe - KX) These normalized electric pulse signals are counted by a scaler 21.

In the same manner, SCA 20 is adjusted so as to produce a normalized electric pulse signal at the output terminal thereof when SCA 20 receives the electric pulse signal corresponding in pulse height to (Zn - KX). These normalized electric pulse signals are counted by a second scaler 22.

Scalers 21 and 22 count the normalized electric pulse signals received from SCA 19 and SCA 20 respectively during a predetermined time period which is controlled by a timer 23. Accordingly, the respective output signal of scalers 21 and 22 are the intensities of (Fe - KX) and (Cn - KX) in the predetermined time period set by the timer 23.

The thickness of the paint 9 on the galvanized plate is solved by the mathematical method described above, by using a computer 24 which receives the counting numbers of scalers 21 and 22 and the time period controlled by the timer 23. The thickness of the paint thus determined is indicated by an electronic digital display 25 which displays the readout of computer 24. The output of the computer 24 is also connected to an external input and output device 26 such as a printer. It will be understood that measurement of the thickness of the paint as thus determined may also be inputted to suitable control apparatus for controlling the amount of paint applied to the galvanized steel plate as it is carried by a conveyor so as to obtain a uniform paint coating.

The method and apparatus of the present invention for measuring the thickness of a layer is applicable not only to measuring the thickness of a paint layer as described, but also to measuring a membrane substance such as wood or vinyl chloride.

Moreover, according to the present invention, in the case of measuring the thickness of a membrane deposited on plated metal, the thickness of the membrane can be measured independently of variation in the thickness of the plating metal without contacting the plating metal or membrane. Accordingly, it is possible to measure precisely the thickness of the membrane portion.

Also, according to this invention, the thickness of the paint is measured continuously on the belt conveyor which carries the painted metal since the measurement is made without contacting the measure object. Accordingly, automation of the painting process can readily be carried out.

What we claim is:

1. A method of measuring the thickness of a non-metallic covering layer on a plated metal plate comprising a metal base plate and a plating metal layer, said method comprising applying to the covered side of said metal plate radiant rays to produce fluorescent X-rays including fluorescent X-rays emitted from said plating metal layer and fluorescent X-rays emitted from said base plate, measuring the intensity of said fluorescent X-rays emitted from said plating metal layer and the intensity of said fluorescent X-rays emitted from said base plate, and deriving the thickness of said covering layer from said intensity of said fluorescent X-rays emitted from said plating metal layer and said intensity of said fluorescent X-rays emitted from said base plate.

2. A method according to claim 1 in which said metal plate is transported by a conveyor and said intensities are measured while said metal plate is being transported by said conveyor.

3. Apparatus for measuring the thickness of a nonmetallic covering layer on a plated metal plate comprising a metal base plate and a plating metal layer, said apparatus comprising an exciting ray source for applying radiant rays to the convered side of said metal plate to produce fluorescent X-rays therefrom including fluorescent X-rays emitted from said plating metal layer and fluorescent X-rays emitted from said base plate, a detector for detecting the fluorescent X-rays emitted by said base plate, an amplifier for amplifying the output of said detector, a discriminator for discriminating between the fluorescent X-rays emitted by said plating metal and the fluorescent X-rays emitted by said base plate, means for measuring the intensities of said fluorescent X-rays emitted by said plating metal and the fluorescent X-rays emitted by said base plate, and computer means receiving the outputs of said intensity measuring means and computing therefrom the thickness of said covering layer.

4. Apparatus according to claim 3, in which said discriminator comprises two single channel analyzers producing output signal pulses corresponding to predetermined pulse heights of signals received from said amplifier.

5. Apparatus according to claim 4, in which said intensity measuring means comprising means for counting pulses received from said single channel analyzers during a determined time period.

6. Apparatus according to claim 3, comprising electronic digital display means for displaying the output of said computer.

7. Apparatus according to claim 6, further comprising printing means for printing the output of said computer.

* * * * *